US005845049A

United States Patent [19]
Wu

[11] Patent Number: 5,845,049
[45] Date of Patent: Dec. 1, 1998

[54] NEURAL NETWORK SYSTEM WITH N-GRAM TERM WEIGHTING METHOD FOR MOLECULAR SEQUENCE CLASSIFICATION AND MOTIF IDENTIFICATION

[75] Inventor: Cathy H. Wu, Tyler, Tex.

[73] Assignee: Board of Regents, The University of Texas System, Austin, Tex.

[21] Appl. No.: 622,351

[22] Filed: Mar. 27, 1996

[51] Int. Cl.$^6$ ............................................. G06F 15/18
[52] U.S. Cl. ........................ 395/22; 706/21; 706/16; 706/25; 706/26
[58] Field of Search ................................. 395/22, 23

[56] References Cited

U.S. PATENT DOCUMENTS

| 5,027,406 | 6/1991 | Roberts et al. | 381/43 |
| 5,449,604 | 9/1995 | Schellenberg et al. | 435/6 |
| 5,619,709 | 4/1997 | Caid et al. | 395/794 |

OTHER PUBLICATIONS

Wu et al. "Gene Classification Artificial Neural System", Proceedings of the First International Symosium on Intelligence in Neural and Biological Systems, IEEE May 1995.
Wu et al. "Classification Artifical Neural Systems for Genome Research", IEEE Super computing, 1992.
Altschul et al., "Issues in Searching Molecular Sequence Databases," Nature Genetics, 6:119, 1994.
Eddy et al., "Maximum Discrimination Hidden Markov Models of Sequence Consensus," Journal of Computational Biology, 2(1):9–23, 1995.
Gribskov et al., "Profile Analysis," Methods in Enzymology, 183:146–159, 1990.
Hirst and Sternberg, "Prediction of Structural and Functional Features of Protein and Nucleic Acid Sequences by Artificial Neural Networks," Biochemistry, 31(32:7211–7218, 1992.
Karlin and Altschul, "Applications and Statistics for Multiple High–Scoring Segments in Molecular Sequences," Proc. Natl. Acad. Sci. USA, 90:5873–5877, 1993.
Krogh et al., "Hidden Markov Models in Computational Biology Applications to Protein Modeling," J. Mol. Biol., 235:1501–1531, 1994.
Sonnhammer and Kahn, "Modular Arrangement of Proteins as Inferred from Analysis of Homology," Protein Science, 3:482–492, 1994.
Wu and Shivakumar, "Back–Propagation and Counter–Propagation Neural Networks for Phylogenetic Classification of Ribosomal RNA Sequences," Nucleic Acids Research, 22(20):4291–4299, 1994.
Wu, "Classification Neural Networks for Rapid Sequence Annotation and Automated Database Organization," Computers Chem., 17(2):219–227, 1993.
Wu et al., "Protein Classification Artificial Neural System," Protein Science, 1:661–677, 1992.

Primary Examiner—George B. Davis
Attorney, Agent, or Firm—Arnold White & Durkee

[57] ABSTRACT

A method for rapid and sensitive protein family identification is disclosed. The new designs include an n-gram term weighting algorithm for extracting local motif patterns, an enhanced n-gram method for extracting residues of long-range correlation, and integrated neural networks for combining global and motif sequence information.

5 Claims, 4 Drawing Sheets

NEURAL NETWORK SYSTEM WITH N-GRAM TERM WEIGHTING METHOD FOR MOLECULAR SEQUENCE CLASSIFICATION AND MOTIF IDENTIFICATION

The government may own rights in the present invention pursuant to grant number R29 LM05524 from the National Library of Medicine.

NOTICE OF COPYRIGHT

A portion of the disclosure of this patent document contains material which is subject to copyright protection. The copyright owner has no objection to the facsimile reproduction by anyone of the patent disclosure, as it appears in the Patent and Trademark Office patent files or records, but otherwise reserves all copyright rights whatsoever.

REFERENCE TO MICROFICHE APPENDIX

A Microfiche Appendix, containing a computer program listing, is attached to this specification. This Microfiche Appendix includes 4 microfiche with a total of 333 frames.

BACKGROUND OF THE INVENTION

1. Field of the Invention

The present invention relates generally to the field of classification of linear sequences into families and in particular to the field of classification of protein and nucleic acid sequences into families based on motif identification using neural networks.

2. Description of the Related Art

As technology improves and molecular sequencing data accumulate nearly exponentially, progress in the Human Genome Project will depend increasingly on the development of advanced computational tools for rapid and accurate annotation of genomic sequences. Currently, a database search for sequence similarities is the most direct computational means of deciphering codes that connect molecular sequences with protein structure and function (Doolittle, 1990). There are good algorithms and mature software for database search and sequence analysis (Gribskov and Devereux, 1991), which may be based on pair-wise comparisons between the query sequence and sequences in the molecular database. These methods range from the most sensitive, but computationally intensive, algorithms of dynamic programming (Needleman and Wunsch, 1970; Smith and Waterman, 1981) to relatively rapid, but less sensitive, methods, such as FASTA (Pearson and Lipman, 1988) and BLAST (Altschul et al., 1990). Alternatively, a database search may be based on information derived from a family of related proteins. This includes methods that screen for motif patterns such as those cataloged in the PROSITE database (Bairoch and Bucher, 1994), the Profile method (Gribskov et al., 1987), the hidden Markov model (HMM) (Krogh et al., 1994; Eddy et al, 1995), and the neural network classification method (Wu et al., 1992).

As a database search tool, the family-based, or classification, approach has two major advantages over the pair-wise comparison methods (Wu, 1993): (1) speed, because the search time grows linearly with the number of sequence families, instead of the number of sequence entries; and (2) sensitivity, because the search is based on information of a homologous family, instead of any one sequence alone. In addition, the classification approach provides automated family assignment and helps to organize second generation databases from which related information can be readily extracted. With the accelerating growth of the molecular sequence databases, it is widely recognized that database searching against gene/protein families or motifs is an important strategy for efficient similarity searching (Altschul et al., 1994). This is evidenced by the growing efforts in recent years to build second generation (or secondary value-added) databases that contain domains, motifs or patterns. Some examples include the SBASE protein domain library (Pongor et al., 1994), the BLOCKS database of aligned sequence segments (Henikoff and Henikoff, 1991), the PRINTS database of protein motif fingerprints (Attwood et al., 1994), and the ProDom protein database (Sonnhammer and Kahn, 1994). While several domain/motif databases are being compiled, there is still a need for the development of database search methods that fully utilize the conserved structural and functional information embedded in those databases to enhance search sensitivity and to more quickly and efficiently extract the useful information contained in newly discovered gene and protein sequences.

It is an object of the present invention to provide improved methods of analyzing sequence database information and newly discovered sequence information by employing a novel motif identification neural design that results in rapid and sensitive protein or gene family identification.

REFERENCES

The following references, to the extent that they provide exemplary procedural or other details supplementary to those set forth herein, are specifically incorporated herein by reference.

Altschul et al., "Basic local alignment search tool," *J. Mol. Biol.*, 215:403–410, 1990.

Altschul et al., "Issues in searching molecular sequence databases," *Nature Genetics*, 6:119–129, 1994.

Attwood et al., "PRINTS: a database of protein motif fingerprints," *Nuc. Acids Res.*, 22:3590–3596, 1994.

Bairoch and Boeckmann, "The SWISS-PROT protein sequence data bank: current status," *Nuc. Acids Res.*, 22:3578–3580, 1994.

Bairoch and Bucher, "Prosite: recent developments," *Nuc. Acids Res., 22:3583–3589, 1994.*

Doolittle, "Searching through sequence databases," *Methods Enzymol.*, 183:99–110, 1990.

Eddy et al., "Maximum Discrimination hidden Markov models of sequence consensus," *J. Comp. Biol.*, 2:9–23, 1995.

Gribskov et al., "Profile analysis: Detection of distantly related proteins," *Proc. Natl. Acad. Sci. USA*, 84:4355–4358, 1987.

Gribskov et al., "Profile analysis," *Methods Enzymol.*, 183:146–159, 1989.

Gribskov and Devereux, *Sequence Analysis Primer*, New York: Stockton Press, 1991.

Henikoff and Henikoff, "Automated assembly of protein blocks for database searching," *Nuc. Acids. Res.*, 19:6565–6572, 1991.

Henikoff and Henikoff, "Protein family classification, based on searching a database of blocks," *Genomics*, 19:97–107, 1994.

Henikoff et al., "Automated construction and graphical presentation of protein blocks from unaligned sequences," *Gene-COMBIS, Gene*, 163:GC17–26, 1995.

Hirst and Sternberg, "Prediction of structural and functional features of protein and nucleic acid sequences by artificial neural networks," *Biochemistry*, 31:7211–7218, 1992.

Karlin and Altschul, "Applications and statistics for multiple high-scoring segments in molecular sequences," *Proc. Natl. Acad. Sci. USA*, 90:5873–5877, 1993.

Krogh et al., "Hidden Markov models in computational biology: applications to protein modeling," *J. Mol. Biol.*, 235:1501–1531, 1994.

Needleman and Wunsch, "A general method applicable to the search for similarities in the amino acid sequences of two proteins," *J. Mol. Biol.*, 48:443–453, 1970.

Pearson and Lipman, "Improved tools for biological sequence comparisons," *Proc. Natl. Acad. Sci. USA*, 85:2444–2448, 1988.

Pearson, "Searching protein sequence libraries: comparison of the sensitivity and the selectivity of the Smith–Waterman and FASTA algorithms," *Genomics*, 11:635–650, 1991.

Pongor et al., "The SBASE protein domain library, release 3.0: a collection of annotated protein sequence segments," *Nuc. Acids. Res.*, 22:3610–3615, 1994.

Sarle, "Neural networks and statistical models," *Proc. 9th Annual SAS Users Group Int'l Conf.*, 1994.

Smith and Waterman, "Comparison of bio-sequences," *Adv. Appl. Math.*, 2:482–489, 1981.

Sonnhammer and Kahn, "Modular arrangement of proteins as inferred from analysis of homology," *Prot. Sci.*, 3:482–492, 1994.

Wallace and Henikoff, "PATMAT: a searching and extraction program for sequence, pattern and block queries and databases," *CABIOS*, 8:249–254, 1992.

Wu et al., "Protein classification artificial neural system," *Prot. Sci.*, 1:667–677, 1992.

Wu, "Classification neural networks for rapid sequence annotation and automated database organization," *Comp. and Chem.*, 17:219–227, 1993.

Wu and Shivakumar, "Back-propagation and counter-propagation neural networks for phylogenetic classification of ribosomal RNA sequences," *Nuc. Acids. Res.*, 22:4291–4299, 1994.

Wu et al., "Neural networks for full-scale protein sequence classification: Sequence encoding with singular value decomposition," *Machine Learning*, 21:177–193, 1995.

SUMMARY OF THE INVENTION

The present invention avoids the drawbacks of prior techniques by providing a rapid and sensitive family classification of linear sequences based on local motif occurrence as well as global sequence similarity. Local motif patterns are extracted by the use of an n-gram term weighting algorithm, and specific terms with long-range correlations are identified using an enhanced n-gram method. The enhanced n-gram method is a way to add in known sequences that have a distant correlation, such as an n-gram containing a gap. A trained neural network is then used to combine global and motif information.

A previous method of using global information was based on the occurrence of n-gram terms in a negative training set and a positive training set (Wu, 1993). These global vectors may then be used to train a neural network to be used for sequence family prediction.

The unique and improved method of the present invention adds a term weighting step so that each n-gram term is modified by a term weighting factor based on the occurrence of each term in a motif sequence and a full length sequence training set. This novel method provides greater selectivity by identifying random occurrences of motif patterns. An additional enhancement of the novel method disclosed herein is the addition of discontinuous terms that are known to be motifs for a particular family that may be added as n-gram terms in the training sets. A further enhancement is the use of integrated neural networks, each trained for a single family so that an unknown sequence may be tested for membership in several families from a single input.

The present invention may be described in certain embodiments as a method of training a neural network to predict membership in a family of linear sequences comprising: (a) providing a training set of full length member sequences, a training set of full length non-member sequences and a training set of family motif sequences; (b) deriving term weights for n-gram terms by dividing the number of occurrences of each n-gram term in the motif set by the number of occurrences in the full length member set; (c) deriving a set of global vectors for the full length member set and a set of global vectors for the full length non-member set using an n-gram method; (d) deriving a set of motif vectors for the full length member set and a set of motif vectors for the full length non-member set by multiplying each term in the global vector set by its term weighting factor; and (e) providing a neural network with multiple output units to represent one family, where the global vector of the member sequence set is used to train the positive full length output unit, the motif vector of the member set is used to train the positive motif output unit, the global vector of the non-member set is used to train the full length negative output unit and the motif vector of the non-member set is used to train the negative motif output unit. This embodiment of the invention may include the step of providing n-gram terms specific for the family as additional input vectors to said neural network.

An embodiment of the invention is also a neural network trained by this method to predict family membership of a linear sequence. In addition, two or more neural networks may each be trained for a different family and then connected so that an unknown sequence may be input to a series of trained neural networks in order to predict family membership.

The present invention may also be described as a method of obtaining term weighted n-grams for use in training a neural network comprising providing a training set of full length member sequences and a training set of family motif sequences and deriving term weights by applying the formula $$W_k = \Sigma M_{ik} / \Sigma F_{ik}$$

to the motif set and the full length set where $W_k$ is the weight factor for the k-th n-gram term in the input vector, and $F_{ik}$ and $M_{ik}$ are total counts of the k-th n-gram term in the i-th sequence of the full-length sequence set and motif set, respectively.

A further embodiment of the present invention is a method of predicting membership of a linear sequence in a family of linear sequences comprising the steps of: (a) obtaining a linear sequence suspected of being a member of said family of sequences; (b) converting the linear sequence into a set of global n-gram terms; (c) obtaining a set of motif terms by applying a term weighting factor to said global n-gram terms; (d) inputting the global terms and the motif terms into a trained neural network as described herein to obtain a full length positive score, a full length negative score, a motif positive score and a motif negative score; (e) computing a probability score from the output scores; and comparing the full length positive score, the motif positive score and the probability score to pre-defined threshold values to predict family membership of the linear sequence.

It is understood that the invention is primarily directed to predicting family membership of amino acid and nucleic acid sequences, but may also be useful for other linear sequences that may be classified into families according to the occurrence of motifs. The methods of prediction may also include providing known n-gram terms specific for the family to both global and motif vectors. These terms may include a motif that includes a large gap for example that would prevent such a motif from being detected by other methods.

The preferred method of obtaining a probability score from the four output scores of the trained neural network is by applying the following formula:

$$\log(P_{hit}/(1-P_{hit})) = \alpha + \beta_1 O_1 + \beta_2 O_2 + \beta_3 O_3 + \beta_4 O_4$$

where $P_{hit}$ is the probability of hit, $\alpha$, $\beta_1$ to $\beta_4$ are the regression parameters, and $O_1$, $O_2$, $O_3$ and $O_4$ are full-length and motif neural network outputs for positive and negative classes, respectively.

It is understood that certain modifications of the disclosed methods may be made that would be encompassed by the spirit and scope of the present claimed invention. For example, one may use various enhanced n-gram methods, which would include, but are not limited to alternative alphabet sets, different n-gram sizes, n-gram terms of various distances, the addition of specific n-gram terms or any combinations of these. In addition, one may alter the enhanced term weighting method to reflect phylogenetic relationships and evolutionary distances among family members, for example.

DETAILED DESCRIPTION

Two techniques provide the basis for the novel method and apparatus contemplated by the present invention. The first technique is a fast, one-step family identification. This first technique replaces pair-wise sequence comparisons in previous systems and techniques. This prior pair-wise technique has the significant disadvantage of a high computational cost. The second technique is the combining of global sequence similarity information with conserved family information embedded in motif patterns to improve search accuracy.

The first concept utilizes an n-gram encoding method to extract global motif information from a sequence. In this method, the test sequence is encoded as a sliding window of n-grams of a pre-determined size. If the n-grams are 4 units in length, then the first four units constitute an n-gram. The window then slides over 1 unit and units 2–5 constitute the next n-gram. This process is continued until the other end of the sequence is reached. Global family correlation is then determined by the number of times each n-gram appears in the sequence. In one embodiment of the present invention, these units are the amino acids of a protein sequence or the nucleic acid bases of a genetic sequence. It is noted, however, that any linear sequence of a defined alphabet can be analyzed by the methods of the present invention. The n-grams from training sequences that are family members (positive training sets) may then be used to train a neural network to evaluate the n-gram inputs from an unknown sequence. From this evaluation, prediction can be accomplished.

One novel and advantageous aspect of the present invention is a significant improvement to an n-gram method of global sequence analysis. This improvement is achieved by providing three new methods to implement the second technique addressed above: (1) an n-gram term weighting algorithm for extracting local motif patterns, (2) an enhanced n-gram method for extracting residues of long-range correlation, and (3) integrated neural networks for combining global and motif sequence information. Motif patterns may be extracted by providing a motif training set of motif sequences positive for a family of sequences. The n-grams as described above are then evaluated for occurrence in the motif set versus occurrence in the entire sequence length. In this way, local motif patterns are recognized and distinguished from more random occurrences of a particular n-gram sequence. The enhanced n-gram method allows known motif sequences for a particular family that are discontinuous to be added into the trained neural network to enhance selectivity of the methods. The enhanced n-gram method, for example, provides the ability to recognize a motif that contains a large gap. This motif would not be recognized by an n-gram method alone. The third technique provides the ability to test a single sequence for membership in a number of families by integrating a series of neural networks, each trained for a particular family.

Figure 1:
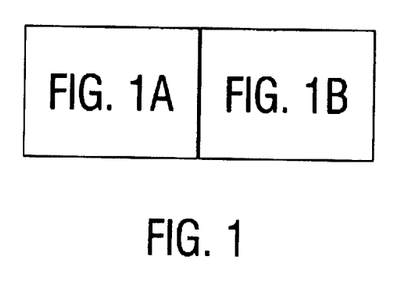
FIG. 1. is a representation of a process of sequence classification, according to the present invention of which the first step is depicted in FIG. 1A and the second and third steps are depicted in FIG. 1B.
Figure 1A:
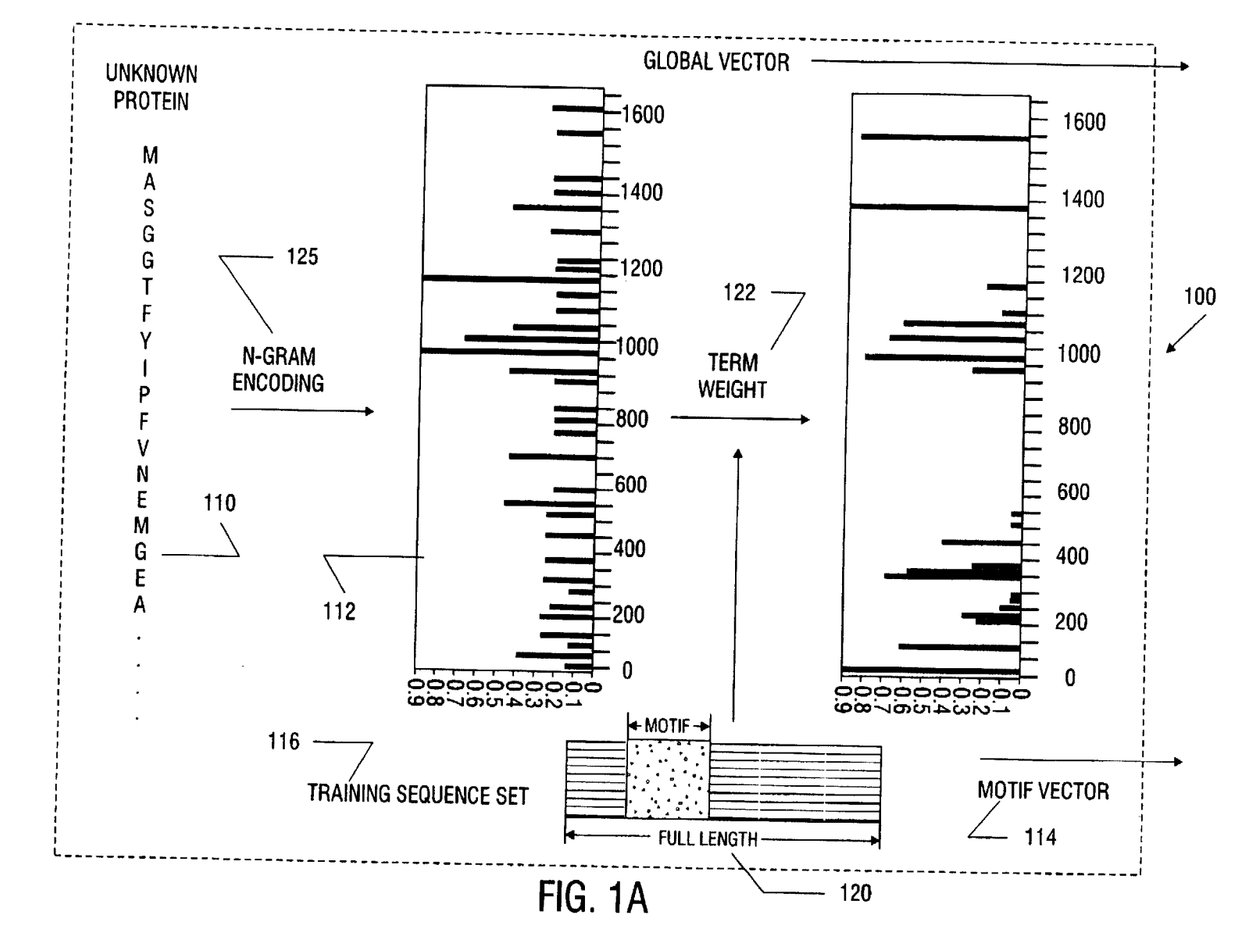
FIG. 1A depicts the sequence encoding step for converting protein or genetic sequences into neural network input vectors.
Figure 1B:
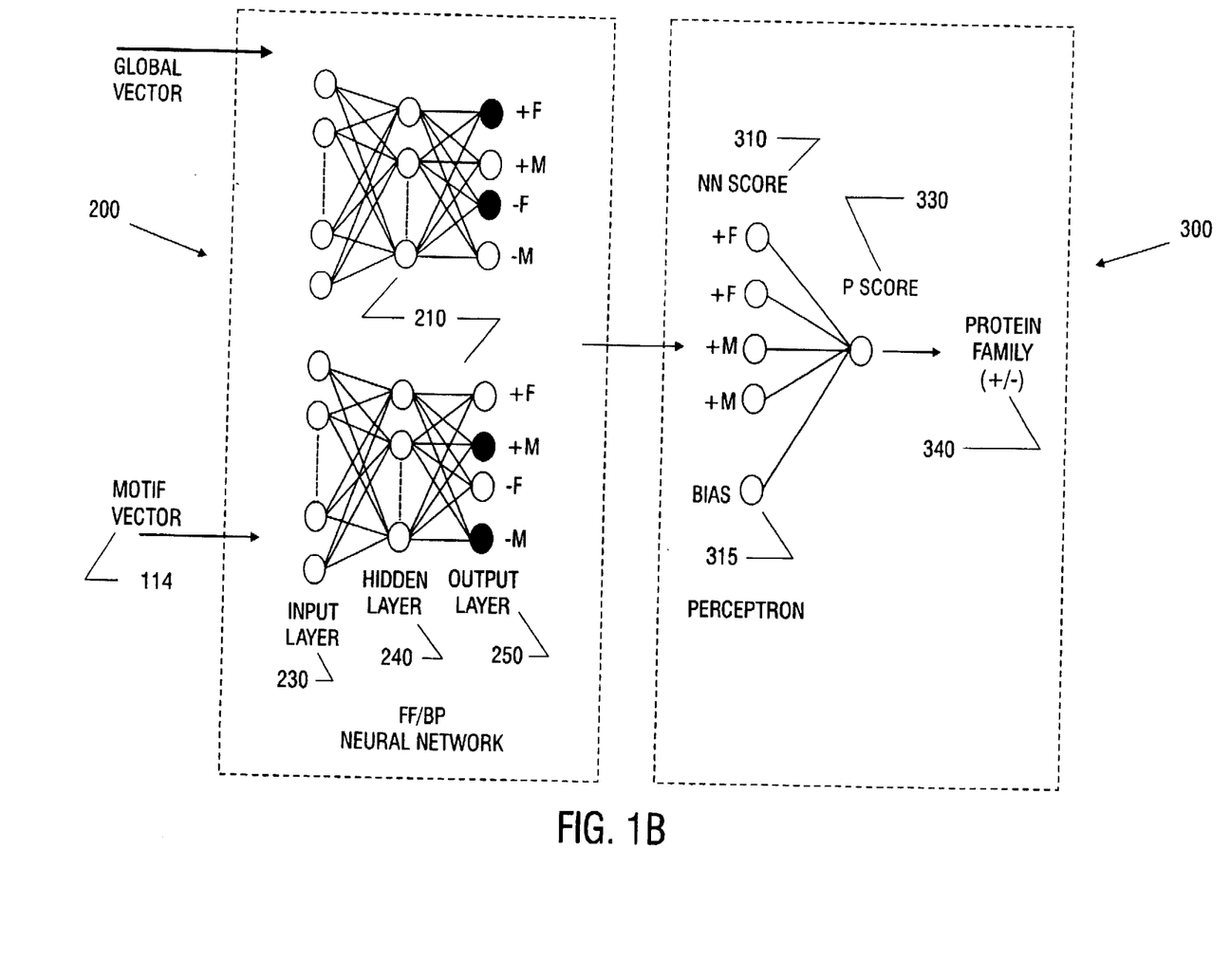
FIG. 1B depict a neural network analysis step analyzing input vectors to determine motif and family output scores, and a classification step for mapping input vectors and output scores to appropriate protein or gene families.

As depicted in FIG. 1A and 1B, the MOTIFIND (MOTIF Identification Neural Design) search involves three steps, a sequence encoding step 100 to convert protein or genetic sequences into neural network input vectors, a neural network analysis step 200 to analyze input vectors to determine motif and family output scores, and classification step 300 to map input vectors and output scores to appropriate protein or gene families.

The sequence encoding scheme 100 involves an n-gram hashing function that extracts and counts the occurrences of patterns (terms) of n consecutive residues (i.e., a sliding window of size n) from a sequence string (Wu, 1993). Unlike the FASTA method, which also uses n-grams (k-tuples), the counts, not the positions, of the n-gram terms along the sequence should be used. By so doing, the method of the present invention is length-invariant, provides certain insertion/deletion invariance, and does not require the laborious sequence alignments of many other prior database search methods. In the encoding, each unit of the neural input vector represents an n-gram term. Thus, the size of the input vector is $m^n$, where m is the size of the alphabet and n is the length of the n-gram. The original sequence string can be represented by different alphabet sets in the encoding, including for protein sequences, the 20-letter amino acids and the six-letter exchange groups derived from the PAM (accepted point mutation) matrix. Different exchange groups can also be defined for different protein families to emphasize the conservative replacement unique for the family.

Looking to FIG. 1, the process of identifying an unknown sequence as a member of a family may be divided into three steps as mentioned above. As shown in FIG. 1A, the first step 100 is to convert the unknown sequence into n-grams that may then be used to derive the neural network input vectors. As shown in FIG. 1B, the second step 200 is to use trained neural networks to convert the n-gram input vectors into neural network scores for both family and motif vectors. As shown in FIG. 1B, the third step 300 is to use a statistical analysis based upon the output scores to make a prediction of family membership.

In the embodiment shown in FIG. 1A, an amino acid sequence of an unknown protein 110 is converted to a series of n-grams through n-gram encoding step 125. Each n-gram is given a numerical score based on the number of occurrences of that n-gram along the unknown sequence. These numerical scores are then used as the global input vector 112. As shown in FIG. 1B, global input vector 112 is then provided as an input to a trained neural network 210. This neural network may be a feed forward, back propagation neural network (FF/BP Neural Network). This n-gram encoding technique may be accomplished using the MOTIFIND program.

A further novel and advantageous technique of the present invention is the use of a term weighting encoding step 122. (FIG. 1A) This term weighting encoding step 122 includes the use of a training sequence set 116 that encompasses the use of a motif training sequence set 118 in addition to the use of a full length training sequence set 120 to create a term weighting factor that is applied in step 122 to the global input vector. The term weighting factor is generated for all n-grams based on the application of an algorithm, which may be the sum of occurrences of the n-gram in the motif training sequence set 118 divided by the sum of occurrences in the full length sequence set 120. The global input vectors 112 are then modified by the term weighting factor in step 122 to create a series of motif vectors 114. The motif input vectors 114 are then also input to a trained neural network 210. (FIG. 1A) This motif termn-weighting technique may be accomplished using the MOTIFIND program.

The trained neural network has an input layer 230, a hidden layer 240, and an output layer 250. (FIG. 1B) The trained neural network is set up to produce four outputs, a positive family score (+F), a negative family score (−F), a positive motif score (+M), and a negative motif score (−M). These neural network outputs provide neural network output scores that may then be subjected to a statistical analysis to produce a probability score (P score) 330. In addition, a bias term 315 may also be considered in determining this probability score 330. This statistical analysis may be provided through the use of a perceptron as discussed in the EXAMPLE below (i.e., "Evaluation Mechanism" section below). The bias 315 relates to the a in the regression formula for the probability score as discussed in the EXAMPLE below. The probability score 330, the +M output score, and the +F output score are then compared to predetermined training scores to derive a negative (−) or positive (+) prediction 340 of family membership.

Figure 2:
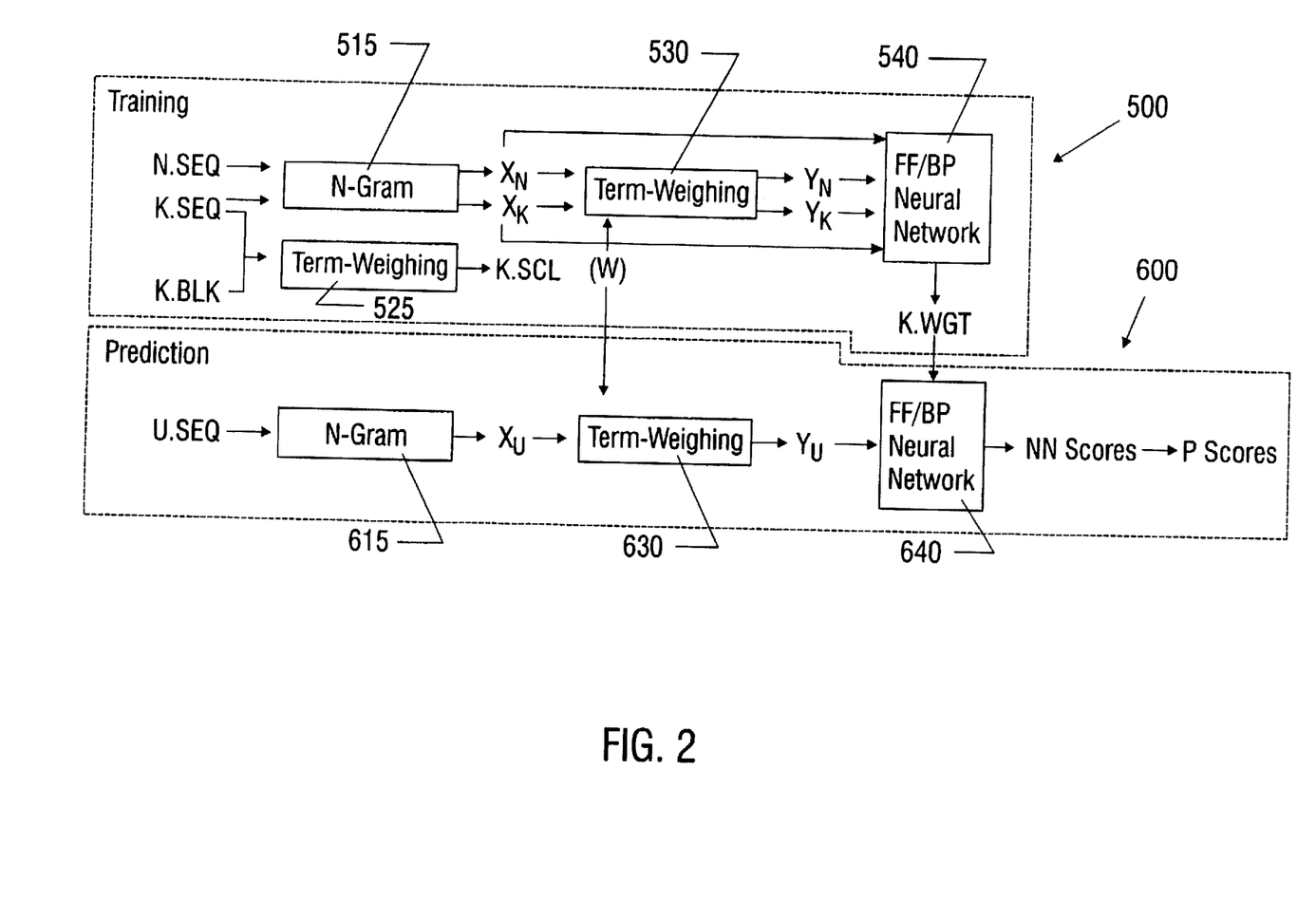
FIG. 2. is a flow diagram of a process of obtaining neural network scores and probability scores to be used in identifying a sequence as a member or non-member of a sequence family, according to the present invention.

Looking now to FIG. 2, a diagram of a training technique 500 and a prediction technique 600 according to the present invention are described. Training technique 500 may be accomplished by training neural networks with known training sequence sets. In the embodiment shown, three sequence sets are provided for the training: (1) N.SEQ, (2) K.SEQ, and (3) K.BLK. N.SEQ represents a full length sequence set in the negative family class. K.SEQ represents a full length sequence set in the positive family class. And, K.BLK represents a motif sequence set of is positive motif sequences in blocks formats.

As further shown in the embodiment shown in FIG. 2, K.SEQ and K.BLK may be used in term waiting step 525 to derive term weighting factor vectors, represented by K.SCL. The term weighting factor vectors may be determined as discussed above. K.SEQ and N.SEQ may then be converted to numerical scores for the positive set information ($X_K$) and negative set information ($X_N$) through n-gram encoding step 515. Both of these sets of n-gram scores may in turn be used as positive and negative global input vectors to train a neural network 540. Neural network 540 may be a feed-forward, back propagation neural network (FF/BP Neural Network). The global vectors of positive sequences ($X_K$) are used to train the +F output unit, and the global vectors of negative sequences ($X_N$) are used to train the −F output unit, as referenced in FIG. 1B. This n-gram encoding technique and global training technique may be accomplished using of the MOTIFIND program.

The present invention further contemplates deriving motif vectors and using them to train a neural network. Through term-weighting application step 530, the motif vectors for both the positive training set ($Y_K$) and the negative training set ($Y_N$) may be computed by applying the term weighting factor (W) from K.SCL to global vector for the positive training set ($X_K$) and the global vector for the negative training set ($X_N$), respectively. Thus, each corresponding global vector is used to compute the numerical score for the n-gram motif vector for the positive set ($Y_K$) and the negative set ($Y_N$). These motif vectors are then used as input vectors to train neural network 540. Optionally, known sequences containing a distance correlation may also be utilized as input vectors. The motif vector for the positive sequences ($Y_K$) is used to train the +M output unit, and the motif vector for the negative sequences ($Y_N$) are used to train the −M output unit. The weights of the neural connections of the trained neural network are then recorded in a file represented by K.WGT. This motif vector derivation technique and motif training technique may be accomplished using of the MOTIFIND program.

Looking to the bottom portion of FIG. 2, a flow diagram of a prediction technique 600 is shown. An unknown sequence represented by U.SEQ is first converted to n-grams vector ($X_U$) through n-gram encoding step 615. In this step, each n-gram of U.SEQ is converted to a numerical score based on the number of occurrences in the sequence. The numerical scores are stored in a file represented by $X_U$. These numerical scores are used as the global input vectors for the unknown sequence. The term weighting factors (W) from K.SCL for each n-gram are applied in motif term-weighting step 630 to the global input vectors ($X_U$) to generate the motif input vectors ($Y_U$) for the unknown sequence. Enhanced n-gram vectors may also be added as both global and motif vector input units. The global input vector ($X_U$) and the motif input vector ($Y_U$) are then input to the trained neural network 640. As also shown in FIG. 1B, neural network scores (NN Scores) are obtained from the neural network for the global family vector scores (+F and −F) and the motif vector scores (+M and −M). The neural network scores may then undergo statistical analysis to compute a probability score (P Score) for each unknown sequence. The family membership may then predicted based on the probability score, the +F vector score and the +M vector score to determine a positive or negative indication of family membership. This indication may be achieved through a comparison of output scores with pre-defined threshold values. For example, if scores are higher than the threshold values, family membership is predicted to be positive. Aspects of the techniques contemplated by the present invention, and depicted in FIGS. 1A, 1B and 2, are now described in further detail.

N-gram Term Weighting and Encoding

A novel n-gram term weighting method may be used to extract conserved family information from motif sequences by multiplying each n-gram with its weight factor. The weight factor is calculated by dividing the total n-gram counts in all motif sequences (term frequency) with total n-gram counts in all full-length sequences of the training set (inverse set frequency), as in:

$$W_k = \Sigma M_{ik} / \Sigma F_{ik}$$

where $W_k$ is the weight factor for the k-th n-gram term in the input vector, and $F_{ik}$ and $M_{ik}$ are total counts of the k-th n-gram term in the i-th sequence of the full-length sequence set and motif set, respectively. The equation illustrates that the n-gram terms of high weights are both conserved (present in all training sequences) with high term frequency, and unique (present in motif regions only) with high inverse set frequency.

Enhanced N-gram Method

The global and motif term vectors, described above, contain "homogenous" n-gram terms. Other specific n-gram terms that are highly conserved can also be included as additional input units (i.e., "heterogeneous" parameters) to the neural networks. These highly conserved terms have strong signals and serve as effective indexes for family identification. The terms may involve neighboring residues, or may involve residues that are far apart in the linear sequence, as frequently found in structural motifs. In the original n-gram method, neighboring letters (with a distance of zero) are extracted. The enhanced methods, on the other hand, use terms of various distances to extract long-range correlation of amino acid residues, thereby, encoding some of the most important positional information that is absent in the original n-gram encoding. For example, the two overlapping histidine heme ligands in the cytochrome b family, R-x(2)-H, H-x(13)-H, R-x(4)-H, H-x(14)-H, can be easily encoded with distances of 2, 13, 4 and 14, respectively.

Integrated Neural Networks

The neural network classification employs three-layered, feed-forward, back-propagation networks (Wu et al., 1992). As a technique for computational analysis, neural network technology has been applied to many studies involving sequence data analysis (Hirst and Sternberg, 1992), such as protein structure prediction, identification of protein-coding sequences, and prediction of promoter sequences. In the Example herein an integrated neural network design is used in which each protein family is represented by an individual neural network with multiple output units, one for each classification parameter.

The size of the input layer is determined by the encoding method. The particular n-gram method described herein used concatenated bi-grams of amino acids and tetra-grams of exchange groups, and resulted in a vector size of 1696 (i.e., $20^2 + 6^4$). Two vectors were generated from each sequence, a global vector and a motif vector (FIG. 1). The global vector contained counts of the n-gram terms from the full-length sequence, scaled between 0 and 1; whereas the motif vector had counts multiplied with weight factors before scaling. The final input vector used for the network training and prediction was generated by concatenating the specific terms (with k units, k may be varied for different families) to both global and motif term vectors (each with 1696 units), having a size of 1696+k. The neural networks used to represent the families had 1696, 1698, and 1696 input units for cytochrome c, cytochrome b and flavodoxin, respectively. The two additional input units in the cytochrome b network were used to represent the long-range information embedded in terms RH2 (i.e., RH n-gram with distance of 2), RH4, and terms HH13 and HH14. The output layer had four units, representing two parameters (global and motif) for two classes (positive and negative sets). The hidden size was determined heuristically to be 20. Therefore, the final network architecture was (1696+k)'20'4. Other network parameters included: random initial weights of −0.3 to 0.3, a back-propagation learning factor of 0.3, a momentum term of 0.2, a constant bias term of −1.0, and an error threshold of 0.01.

The following examples are included to demonstrate preferred embodiments of the invention. It should be appreciated by those of skill in the art that the techniques disclosed in the example which follows represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

The neural networks used in the practice of the present invention may also, in light of the present disclosure, be designed to include various numbers of hidden layers of various sizes, or the number of output units may be varied to reflect additional classification parameters. The training sets may also be enhanced, by increasing the number of motifs and their lengths, for example, or by the addition of structural motifs

EXAMPLE

MOTIFIND Implementation

Computer program listings of subroutines that may be used in the practice of the methods and apparatuses disclosed herein are attached to this specification as a Microfiche Appendix. Of these listings, the subroutine entitled ngram.c may be used to determine global vectors; a subroutine entitled nnt-bp.c may be used to encode a three-layered feed forward back-propagation neural network; a subroutine entitled nnp-bp.c may be used to encode a neural network for predicting family membership of a linear sequence; a subroutine forward.c may be used as a feed forward application of the neural network; and backward.c may be used as a back propagation application for a neural network. Other subroutines are also included that perform various other functions for training a neural network and for using the trained neural network for prediction.

The MOTIFIND system has been coded with C programs and implemented on the Cray Y-MP (UNICOS) supercomputer of the University of Texas System and a DEC Alpha workstation (OSF/1), using a program structure similar to GenCANS (GenCANS is presently available from World Wide Web at http://diana.uthct.edu/). The system software has three general components: (1) a preprocessor to create the training and prediction patterns from input sequence files, (2) a neural network program to classify input patterns, and (3) a post-processor to perform statistical analysis and summarize classification results.

Data Sets

Three protein families of electron transferases, cytochrome c, cytochrome b and flavodoxin, were used to test the system (Table 3). The three families represent three different case studies. The cytochrome c family, grouped according to PROSITE pattern PS00190 and whose members share the same C-x-x-C-H heme-binding site signature, actually is a widely diversified family that consists of cytochrome c,c', c1 to c6, c550 to c556, cytochrome f and reaction center cytochrome c. The family members vary greatly in their lengths, which range from about 85 aa (amino acids) in cytochrome c5 and c6, to more than 300 aa in cytochrome f and some precursors. The size of different protein groups within the family also varies, from the most abundant cytochrome c (85 entries) to small groups such as cytochrome c553 (less than 5 entries). Both cytochrome b and flavodoxin families, on the other hand, are more homogenous. The cytochrome b family has two subgroups, the cytochrome b of around 380 aa long and b6 of about 220 aa. The flavodoxin is a small, homogenous family containing only 23 members.

The positive set consisted of all sequences of the protein family studied, Table 3. These included the sequences cataloged in the PROSITE database (Release 12.2, February 1995, compiled based on SwissProt database Release 29.0), as well as new sequences selected directly from the SwissProt database (Release 31.0, February 1995) (Bairoch and Boeckmann, 1994) by combinations of database sequence search, signature pattern search and manual examination of sequence annotation. The complete negative set contained all sequences in the SwissProt database that were non-members of the protein family studied, Table 3).

The training set for the neural network consisted of both positive (members of the protein family) and negative (non-members) patterns at a ratio of 1 to 2. Approximately two-thirds of the "T" sequences (true positives) cataloged in PROSITE were chosen randomly as the positive training set. The negative training set was selected randomly from all non-members. Two prediction sets were used, one full-scale and one small-scale. The full-scale prediction set was the entire SwissProt database (Release 31.0), containing 43,470 sequences. The small prediction set consisted of all positive patterns and randomly selected negative patterns. For cytochrome b and flavodoxin, all "F" sequences (false positives) in the PROSITE database were also included as negative patterns. In MOTIFIND, the neural network training uses both full-length and motif sequences to obtain global and local information. The full-length sequences were directly taken from the SwissProt database. The motif sequences used to compute the n-gram weight factors were compiled by using a string pattern-matching program to search for PROSITE signatures (Table 3) and retrieve substrings in the BLOCKS format (Henikoff and Henikoff, 1991).

To ensure the validity of the MOTIFIND results, the cross-validation method was used. In this method, the positive training set for each family was randomly divided into three approximately equal sized sets. In each trial, one set was used for prediction and the remaining two sets for training. Since similar results were obtained using any of the three data sets for each protein family, only dataset one was used for all comparative studies described below.

Evaluation Mechanism

The system performance was evaluated based on speed (CPU time) and predictive accuracy. Accuracy was measured in terms of both sensitivity (ability to detect true positives) and specificity (ability to avoid false positives) at different threshold values. Two types of scores were given to each query sequence after network prediction, the neural network score and the probability (P) score. There were four neural network outputs, and two of these (i.e., +F and +M scores, FIG. 1B) were used for scoring. The P score was computed using a logistic regression function:

$$\log(P_{hit}/(1-P_{hit})) = \alpha + \beta_1 O_1 + \beta_2 O_2 + \beta_3 O_3 \beta_4 O_4$$

where $P_{hit}$ is the probability of hit, $\alpha$ and $\beta_1$ to $\beta_4$ are the regression parameters, and $O_1$, $O_2$, $O_3$ and $O_4$ are full-length and motif neural network outputs for positive and negative classes, respectively (i.e., +F, +M, -F and -M scores, FIG. 1B). The logistic regression model is equivalent to a two-layered neural network (i.e., perceptron) with a logistic activation function (Sarle, 1994). The two-layer perceptron was implemented by adopting the same feed-forward and back-propagation functions (Wu et al., 1992). The perceptron had four input units (which used $O_1$ to $O_4$ as inputs) and one output unit (whose score was $P_{hit}$, as well as a bias term (for computing the constant, $\alpha$).

A positive sequence is considered to be accurately predicted (i.e., true positive) if both the P score and the average neural network score (i.e., the average of the +F and +M scores) are higher than certain pre-determined threshold values. Conversely, a negative (non-member) sequence is accurately predicted (ie., true negative) if either score is lower than the threshold. Note that both neural network scores and P scores range between 0.0 (no match) and 1.0 (perfect match). The SSEARCH program (version 1.7A, July 1994) (Smith and Waterman, 1981; Pearson, 1991) was used to determine the overall sequence similarity of a query sequence to the neural network training sequences. The program was part of the FASTA package available from the FTP server (ftp.virginia.edu) and implemented on a DEC alpha workstation.

Comparative Studies

The MOTIFIND results were compared to those obtained by several other existing methods, including the BLAST database search, the PROSITE pattern search, the BLIMPS search of BLOCKS, the HMM method, and the PROFILESEARCH.

The BLAST search was performed using the improved version (version 1.4, October 1994) that adopted Sum statistics (Karlin and Altschul, 1993). The program was obtained from the NCBI FTP server (ncbi.nlm.nih.gov) and implemented on a DEC workstation. The same training set (containing both positive and negative sequences) and the prediction set used in MOTIFIND (Table 3) were used as BLAST database and query sequences. The negative set was included as database entries for the BLAST search because it provided much better class separation for BLAST. The result reported was based on the probability score of the first-hit (i.e., the hit with the highest score).

The PROSITE search was performed by using a string pattern-matching program to search for PROSITE signatures. The results obtained with the pattern-matching program using the SwissProt database Release 29.0, were identical to those cataloged in the PROSITE database (Release 12.2). In PROSITE, the sequences are categorized as "T" (true positive containing signature), "N" (false negative containing degenerated motif not detectable by signature), "P" (false negative lacking motif region, mostly fragmentary), "?" (unknown containing signature), and "F" (false positive containing signature).

The BLIMPS search involved three steps, BLOCKS building using PROTOMAT (Henikoff and Henikoff, 1991), search against individual BLOCKS using BLIMPS (Wallace and Henikoff, 1992), and BLOCKS group analysis using BLKSORT (Henikoff and Henikoff, 1994) if there are multiple BLOCKS in a family. To obtain the BLOCKS, the training sets (containing only positive sequences) were sent directly to the BLOCKMAKER (version 1.11, June 1994) E-Mail server (blockmaker@howards.fhcrc.org) (Henikoff et al., 1995). Three BLOCKS were returned from the server for the cytochrome c training set, the GCH motif (13 aa long), the GGG motif (13 aa) and the Gibbs (10 aa, identical to GCH motif but shorter); one BLOCKS returned for cytochrome b, Gibbs (53 aa); and two identical BLOCKS returned for flavodoxin, TAI motif (20 aa) and Gibbs (20 aa). The individual BLOCKS were then used to search the prediction set with BLIMPS (version 2.2 A, May 1994) obtained from the NCBI server, using default amino acid frequency. Among the three BLOCKS for the cytochrome c family, GCH motif and Gibbs gave similar results and were much better than the GGG motif. The GCH and GGG motifs were combined in the BLKSORT program (version 1.5, October 1994) to incorporate global information (Henikoff and Henikoff, 1994), however, no improvement was found in the overall predictive accuracy. Therefore, only Gibbs results are presented in the comparative study for all three protein families.

There are two programs available for running the hidden Markov model, HMMER (ftp://genome.wust1.edu/pub/eddyl) and SAM (ftp://ftp.cse.ucsc.edu/pub/protein). Both were implemented and tested; but only HMMER was used in the comparative study, since it gave better predictive accuracy and ran faster than SAM. There were two steps in using the HMMER (version 1.8, April 1995): model building from unaligned training sequences (positive sequences in the neural network training sets) using the HMMT program, and a Smith-Waterman database search against the model using the HMMSW program. The HMM method can be used for a database search of whole proteins or protein domains. Both global and motif models were built for cytochrome c because it is a family with widely divergent members; and only global models were used for the more homogeneous families of cytochrome b and flavodoxin. The global and motif models were built with the same full-length and motif training sequences used in MOTIFIND. The lengths of the resulting models were 124 aa, 17 aa, 381 aa and 172 aa, respectively, for the cytochrome c global and motif models, the cytochrome b global model, and the flavodoxin global model.

The profile method was conducted using the GCG Wisconsin Sequence Analysis Package (version 8.0, September 1994), running on a VAX mainframe. There were three procedures: multiple sequence alignment of training sequences using the PILEUP program, profile generation from the resulting alignment using the PROFILEMAKE program, and a database search against each profile using the PROFILESEARCH program (Gribskov et al., 1989). Default parameters were used in all the programs. As with the HMM method, the profile method can also be used for searching protein families or domains. Profiles used in the comparative studies and their lengths were: motif profile for cytochrome c (15 aa), global and motif profiles for cytochrome b (505 and 41 aa) and global profile for flavodoxin (186 aa). All profiles were made from the same full-length and motif sequences used in MOTIFIND, except that, for cytochrome c, only 100 (instead of 149) sequences were selected because of the size limitation of the PROFILEMAKE program.

MOTIFIND Performance

Table 1 shows that MOTIFIND achieved 100% sensitivity and more than 99.6% specificity in a full-scale SwissProt database search for all three protein families studied. There are several factors that may affect the predictive accuracy of a given sequence: (1) the degree of overall sequence similarly, (2) the sequence length, (3) the prevalence of the sequence in the family, and (4) the existence of a motif region. MOTIFIND is capable of identifying not only full-length, closely-related sequences, but also distantly related sequences, fragmentary sequences, and sequences of under-represented groups within the family. Close inspection of sequence patterns and their scores reveals that MOTIFIND can detect with high scores the distantly related sequence that has a low degree of overall sequence similarity, but a conserved motif region. Examples include CYC4_PSEAE (31.8% identify in an 85 aa overlap), CYCL_PARDE (26.5% in 68 aa overlap) and CYB_TRYBB (28.0% identify in 346 aa overlap), all of which have a P score of 0.99 (Table 2). MOTIFIND is robust in identifying fragmentary sequences, even those that contain only partial motifs or lack the complete motif region, although at a lower score. Examples include CYC_TRYBB, CYB_RABIT, CYB_RANCA, and FLAW_AZOCH (Table 2). Sequences belonging to under-represented subgroups can also be readily detected, as seen in many cytochrome c entries such as CY2_RHOGE, CYCP_RHOGE and CY4C_PSEPU. MOTIFIND is shown herein to work well with small families (i.e., the training set for flavodoxin had only 14 sequences). In fact, it worked equally well with as little as five to ten sequences. Furthermore, preliminary studies with several additional protein families, including cytochrome P450, ferredoxin, thioredoxin and immunoglobulin, all yielded similar predictive accuracy, indicating that MOTIFIND is generally applicable to other proteins.

The training of the neural networks was fast, ranging from 10 to 50 CPU minutes in the DEC alpha workstation for each family. The training time is proportional to the number of neural interconnections (i.e., number of weights to be determined) and the number of training sequences. The prediction also ran fast, averaging about 0.03 CPU seconds on the workstation for each sequence. The prediction time is dominated by the preprocessing time (i.e., more than 95% of the total time), and should remain constant regardless of the database size. The time required for preprocessing query sequences is determined by the sequence length and the size of the n-gram vectors, but independent of the number of training sequences.

Comparative Analysis

The accuracy of MOTIFIND is comparable to that of BLAST, but at a significantly faster speed (Table 1). On the workstation, the complete SwissProt database search by BLAST took between six to ten CPU hours, depending on the number of database sequences (training sequences). But it took less than 25 minutes (including preprocessing and post-processing time) with MOTIFIND, a 20 fold increase in speed. MOTIFIND is better than BLAST for identifying short fragmentary sequences containing specific motifs, or distantly related sequences that bear little overall sequence similarity other than the motif regions. The latter is seen in the cytochrome c family.

MOTIFIND is much more sensitive than the PROSITE search, which is based on simple signature patterns to detect family members and runs very fast (Table 1). PROSITE searches fail to identify motif sequences that are not completely conserved, as defined by the PROSITE signature patterns (i.e., "N" patterns, Table 2); whereas the neural network system disclosed herein is noise tolerant and excellent in handling ambiguous motif patterns. The PROSITE search also fails to detect partial sequences that do not contain specific motifs (i.e., "P" patterns, Table 2); but such detection is possible in MOTIFIND with the incorporation of global information.

The BLIMPS search of BLOCKS also runs fast and is sensitive in detecting family members containing conserved motifs. The method, however, fails to recognize all fragmentary sequences that lack motif regions, including CYC_TRYBB, CYB_RABIT and CYB_RANCA, as one would expect. Furthermore, like the PROSITE search, the number of false positives increases when the BLOCKS/motif length is short, as found in the cytochrome c family. Many false positives returned by the PROSITE search ("F" patterns) are also seen in the BLIMPS search result, including FDHB_WOLSU, POLG_HCVKB, UROM_HUMAN and YM91_SCHPO (Table 2).

The HMM method can be used for database searching of whole proteins or domains. The search using global models is about five to eight times slower than MOTIFIND, as seen in the cytochrome b and flavodoxin families, because it involves the Smith-Waterman search. The global model is less sensitive in detecting distantly related sequences, such as CYB_PARTE (24.5% identity in a 351 aa overlap), or fragmentary sequences, such as FLAW_AZOCH (17 aa long) (Table 2). The global model of cytochrome c also misses several members of the under-represented groups, including CY2_RHOGE, CY3_DESVM, CYCP_RHOGE and C554_CHLAU. In contrast, the HMM motif model is more sensitive in detecting the widely diversified members of the cytochrome c family at a much lower false positive rate (Table 1). The motif model (with a model length of 17 aa) also runs much faster, because the search time is directly proportional to the model length. The motif model, however, cannot detect fragmentary sequences without motif regions (e.g., CYC_TRYBB), like the BLIMPS search. Furthermore, the motif model is still weak in recognizing members of under-represented groups, as reflected by the low scores of many entries and the missed CYCL_PARDE pattern (Table 2).

The PROFILESEARCH of global profiles is less sensitive, mainly because all short fragments were given low scores, often below cut-off threshold values selected for acceptable specificity. Examples include FLAW_AZOCH (17 aa) (Table 2) and several members of the cytochrome b family such as CYB_THOTO (79 aa). The score can be normalized in relationship to sequence length and used to compute a Z-score if there are more than 400 sequences in the prediction set. However, the use of Z-scores only improves the predictive results marginally, because many sequence fragments become false positives. Therefore, motif profiles were used in PROFILESEARCH to study both cytochrome c and b families. The results show that it is less sensitive and specific than other motif-based methods, including MOTIFIND, BLIMPS and the HMM motif model (Tables 1 and 2).

TABLE 1

Comparison of MOTIFIND with other database search and family identification methods in terms of speed and accuracy.

| Protein Family | Search Method | CPU Time[a] | Sensitivity[b] (%) | True+ | Specificity F[b] (%) | False+ | Specificity S[b] (%) | False+ |
|---|---|---|---|---|---|---|---|---|
| Cytochrome C | MOTIFIND | 984 | 100.00 | 238 | 99.61 | 167 | 100.00 | 0 |
|  | BLAST | 35,116 | 100.00 | 238 | 99.08 | 396 | 99.38 | 1 |
|  | PROSITE | 27 | 97.07 | 231 | 99.46 | 233 | 97.53 | 4 |
|  | BLIMPS | 172 | 99.58 | 237 | 98.49 | 653 | 97.53 | 4 |
|  | HMM Motif | 426 | 99.16 | 236 | 98.82 | 510 | 98.77 | 2 |
|  | HMM Global | —[c] | 97.48 | 232 | — | — | 91.98 | 13 |
|  | PROFILE Motif | — | 99.16 | 236 | — | — | 96.30 | 6 |
| Cytochrome B | MOTIFIND | 1,452 | 100.00 | 151 | 99.95 | 23 | 100.00 | 0 |
|  | BLAST | 24,597 | 100.00 | 151 | 99.99 | 3 | 100.00 | 0 |
|  | PROSITE | 33 | 96.69 | 146 | 100.0 | 1 | 99.01 | 1[d] |
|  | BLIMPS | 756 | 98.68 | 149 | 99.86 | 60 | 100.00 | 0 |
|  | HMM Global | 11,740 | 99.34 | 150 | 99.97 | 14 | 100.00 | 0 |
|  | PROFILE Motif | — | 98.01 | 148 | — | — | 100.00 | 0 |
|  | PROFILE Global | — | 98.68 | 149 | — | — | 88.12 | 12 |
| Flavodoxin | MOTIFIND | 1,019 | 100.00 | 23 | 99.99 | 5 | 100.00 | 0 |
|  | BLAST | 21,411 | 100.00 | 23 | 99.95 | 23 | 100.00 | 0 |
|  | PROSITE | 34 | 91.30 | 21 | 99.99 | 5 | 76.19 | 5[d] |
|  | BLIMPS | 265 | 100.00 | 23 | 99.99 | 6 | 100.00 | 0 |
|  | HMM Global | 5,896 | 100.00 | 23 | 99.96 | 18 | 95.24 | 1 |
|  | PROFILE Global | — | 91.30 | 21 | — | — | 90.48 | 2 |

[a]The time shown is the total CPU seconds required on a DEC alpha workstation to process the entire production set of 43,470 sequences.
[b]The sensitivity is the percentage of true positives (True+) over the total number of positive patterns in the prediction set. The Specificity is 1 - the percentage of false positives (False+) over the total number of negative patterns in the prediction set. Specificity F = Specificity of the full-scale production set; Specificity S = Specificity of the small prediction set.
[c]The full-scale prediction was not run.
[d]The specificity of PROSITE is arbitrarily low in these two prediction sets because all of the "F" (false positive) patterns identified in PROSITE were included.

TABLE 2

Comparative prediction score results of MOTIFIND and other methods for selected sequence patterns[a]

| Sequence ID | Sequence Length | ProSite[b] | BLAST | MOTIFIND[c] Global/Motif | Prob. | BLIMPS | HMM Global | HMM Motif | Profile[d] |
|---|---|---|---|---|---|---|---|---|---|
| Cytochrome C | | | | | | | | | |
| CYC_HORSE | 104 | T | 7.0e−75 | 1.00/1.00 | 0.99 | 473 | 261.42 | 35.16 | 5.72 |
| CY2_RHOGE | 85 | T | 4.8e−26 | 0.26/0/93 | 0.65 | 370 | 0 | −0.79 | 4.75 |
| CYC3_DESVM | 107 | T | 3.7e−74 | 0.98/1.00 | 0.99 | 362 | 0 | 0.45 | 4.37 |
| CYC4_PSEAE | 181 | T | 2.3e−05 | 1.00/1.00 | 0.99 | 363 | −0.36 | 3.28 | 4.92 |
| CYCP_RHOGE | 129 | T | 6.4e−28 | 0.82/1.00 | 0.97 | 343 | 0 | −1.12 | 4.67 |
| C554_CHLAU | 414 | T | 5.1e−14 | 0.01/0.99 | 0.44 | 354 | 0 | 0.31 | 4.63 |
| CYCL_PARDE | 177 | T | 2.4e−04 | 0.99/0.99 | 0.99 | 345 | −4.43 | 0 | 5.22 |
| CY4C_PSEPU | 78 | T | 6.7e−03 | 0.72/0.92 | 0.96 | 354 | −4.80 | 2.34 | 4.94 |
| NIRT_PSEST | 201 | T | 8.5e−83 | 0.89/1.00 | 0.99 | 344 | −6.47 | 0.73 | 4.73 |
| CYC_CRIFA | 113 | N | 5.0e−45 | 1.00/1.00 | 0.99 | 339 | 174.32 | 20.45 | 4.27 |
| CYC_EUGVI | 102 | N | 1.2e−43 | 0.99/1.00 | 0.99 | 295 | 160.99 | 7.37 | 4.01 |
| CY1_EUGGR | 243 | N | 4.2e−85 | 0.07/0.99 | 0.50 | 287 | −5.05 | 3.68 | 0 |
| CYC_TRYBB | 93 | P | 4.2e−36 | 0.99/0.00 | 0.59 | 0 | 135.30 | 0 | 0 |
| FDHB_WOLSU | 200 | F | 0 | 0 | 0 | 330 | 0 | −1.28 | 4.26 |
| POLG_HCVBK | 3010 | F | 0 | 0 | 0 | 316 | 0 | 0 | 4.64 |
| UROM_HUMAN | 640 | F | 0 | 0 | 0 | 327 | 0 | 0 | 4.40 |
| YM91_SCHPO | 807 | F | 0 | 0 | 0 | 326 | 0 | 0 | 4.50 |
| CYNT_ECOLI | 218 | — | 0 | 0 | 0 | 0 | 0 | −1.08 | 0 |
| GLBL_CHITP | 161 | — | 0 | 0 | 0 | 0 | −0.06 | 0 | 0 |
| THYP_HUMAN | 101 | — | 1.1e−08 | 0 | 0 | 0 | 0 | 0 | 0 |
| Cytochrome B | | | | | | | | | |
| CYB_BOVIN | 379 | T | 6.0e−268 | 0.99/1.00 | 0.99 | 3373 | 1193.2 | —[e] | 26.65 |
| CYB6_MAIZE | 215 | T | 1.3e−157 | 0.99/0.99 | 0.99 | 2421 | 352.10 | — | 18.41 |
| CYB_TRYBB | 363 | T | 1.2e−55 | 0.96/0.91 | 0.99 | 948 | 73.42 | — | 12.26 |
| CYB_PARTE | 391 | N | 1.4e−22 | 0.73/0.42 | 0.86 | 952 | 0 | — | 0 |
| CYB_SULAC | 563 | N | 7.3e−27 | 0.47/0.69 | 0.46 | 1366 | 28.83 | — | 12.26 |
| CYB_RABIT | 169 | P | 1.4e−106 | 0.88/0.04 | 0.77 | 0 | 465.64 | — | 0 |
| CYB_RANCA | 114 | P | 1.4e−61 | 0.96/0.01 | 0.74 | 0 | 277.60 | — | 0 |
| YO43_CAEEL | 1040 | F | 0 | 0 | 0 | 0 | 0 | — | 0 |
| Flavodoxin | | | | | | | | | |
| FLAV_ANASP | 169 | T | 3.7e−122 | 0.99/0.99 | 0.99 | 1056 | 247.49 | —[e] | 52.25 |
| FLAV_MEGEL | 137 | T | 2.2e−96 | 0.99/0.99 | 0.99 | 955 | 69.01 | — | 31.31 |
| FLAW_ECOLI | 173 | N | 1.2e−61 | 0.94/0/97 | 0.97 | 817 | 139.16 | — | 42.89 |
| FLAW_AZOCH | 17 | P | 9.0e−05 | 0.00/0.97 | 0.89 | 676 | 2.01 | — | 0 |
| HEMG_ECOLI | 181 | F | 0 | 0 | 0 | 0 | 9.21 | — | 0 |
| ATPA_MOUSE | 553 | — | 0 | 0 | 0 | 0 | 0 | — | 32.22 |

[a]Only scores that are higher than the threshold values are shown; all other results are given a score of 0. Different cut-off scores were selected for every method in order to optimize the sensitivity and specificity of each given method.
[b]The PROSITE codes are: "T" (true positive), "N" (false negative containing degenerate signature), "P" (false negative lacking signature), "F" (false positive), and "—" (true negative).
[c]The MOTIFIND scores shown are: "Global" (global neural network score, i.e., = F score, FIG. 1), "Motif" (motif neural network score, i.e., + M score), and "Prob" (probability or P score).
[d]The PROFILESEARCH results shown are the motif profile results for cytochrome c and b, and global profile results for flavodoxin.
[e]The prediction was not run.

TABLE 3

Data sets for neural network training and prediction

| Protein Family | PROSITE Number | Motif Length[a] | Training Set # Pos[b] | Training Set # Neg[b] | Prediction Set # Pos | Prediction Set # Neg F[b] | Prediction Set # Neg S[b] |
|---|---|---|---|---|---|---|---|
| Cytochrome C | PS00190 | 15 | 149 | 298 | 238 | 43,232 | 162 |
| Cytochrome B | PS00192 | 41 | 86 | 172 | 151 | 43,319 | 101 |
| Flavodoxin | PS00201 | 19 | 14 | 28 | 23 | 43,447 | 21 |

[a]The motif patterns, adopted from PROSITE signatures, are: x(8)-C-{CPWHF}-{CPWR}-C-H-{CFYW}-x (Cytochrome C); x(9)-{DENQ}-x(3)-G-{FYWM}-x-{LIVMF}-R-x(2)-H-x(13)-H-x(6) (Cytochrome B); and x(2)-|LIV|-|LIVFY|-|FY|-x-|ST|-x(2)-|AG|-x-T-x(3)-A-x(2)-|LIV| (Flavodoxin).
[b]# Pos = Number of positive patterns; # Neg = Number of negative patterns; Neg F = Negative patterns in the full-scale prediction set, i.e., all negative sequences in the entire SwissProt database; Neg S = Negative patterns in the small-scale prediction set.

While the compositions and methods of this invention have been described in terms of preferred embodiments, it will be apparent to those of skill in the art that variations may be applied to the methods and in the steps or in the sequence of steps of the methods described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for training a neural network to predict membership in a family of linear sequences comprising;
    providing a training set of full length member sequences, a training set of full length non-member sequences and a training set of family motif sequences;
    deriving term weights for n-gram terms by dividing the number of occurrences of each n-gram term in the motif set by the number of occurrences in the full length member set;
    deriving a set of global vectors for the full length member set and a set of global vectors for the full length non-member set using an n-gram method;
    deriving a set of motif vectors for the full length member set and a set of motif vectors for the full length non-member set by multiplying each term in the global vector set by its term weighting factor;
    providing a neural network with multiple output units to represent one family;
    using the global vector of the member sequence set to train the positive full length output unit;
    using the motif vector of the member set to train the positive motif output unit;
    using the global vector of the non-member set to train the fall length negative output unit; and
    using the motif vector of the non-member set to train the negative motif output unit of said neural network.

2. The method of claim 1, further defined as comprising the step of providing n-gram terms specific for said family as additional input vectors to said neural network.

3. A neural network trained by the method of claim 1 to predict family membership of a linear sequence.

4. A series of connected neural networks, wherein each network is trained for a particular family by the method of claim 1.

5. A method of obtaining term weighted n-grams for use in training a neural network comprising:
    providing a training set of full length member sequences and a training set of family motif sequences; and
    deriving term weights by applying the formula $$W_k = \Sigma M_{ik} / \Sigma F_{ik}$$

to said motif set and said full length set, where $W_k$ is the weight factor for the k-th n-gram term in the input vector, and $F_{ik}$ and $M_{ik}$ are total counts of the k-th n-gram term in the i-th sequence of the full-length sequence set and motif set, respectively.

* * * * *

UNITED STATES PATENT AND TRADEMARK OFFICE
CERTIFICATE OF CORRECTION

PATENT NO.  : 5,845,049

DATED       : December 1, 1998

INVENTOR(S) : Cathy H. Wu

It is certified that error appears in the above-identified patent and that said Letters Patent is hereby corrected as shown below:

In claim 1, column 19, line 22, delete "fall" and insert --full-- therefor.

Signed and Sealed this

Ninth Day of March, 1999

Attest:

Q. TODD DICKINSON

Attesting Officer

Acting Commissioner of Patents and Trademarks